United States Patent [19]

LaRue et al.

[11] 4,297,992
[45] Nov. 3, 1981

[54] DISTAL JOINT FINGER SPLINT

[76] Inventors: Maureen L. LaRue, 3 Eagle Rock Trail, Ormond Beach, Fla. 32074; Richard R. Larsen, 1308 Laurel Dr., Daytona Beach, Fla. 32017

[21] Appl. No.: 91,587

[22] Filed: Nov. 5, 1979

[51] Int. Cl.³ ............................................. A61F 5/10
[52] U.S. Cl. ................................. 128/77; 128/87 A; 434/166
[58] Field of Search ............. 128/77, 87A, 26; 35/36, 35/37; 248/118.1, 118.3, 118.5; 434/166

[56] References Cited

U.S. PATENT DOCUMENTS

| | | | |
|---|---|---|---|
| 705,920 | 7/1902 | Gottschalk | 35/36 |
| 1,917,794 | 7/1933 | Brown | 128/77 |
| 4,243,026 | 1/1981 | Barber | 128/77 |

FOREIGN PATENT DOCUMENTS

| | | | |
|---|---|---|---|
| 333911 | 11/1918 | Fed. Rep. of Germany | 128/77 |
| 4564 | of 1908 | United Kingdom | 35/36 |
| 100360 | 6/1916 | United Kingdom | 35/37 |

OTHER PUBLICATIONS

Glanville, H. J., "New Inventions" In the Lancet, 2/3/62, pp. 252-253.
Orthopaedic Appliance Atlas, vol. I, Pub.-J. W. Edwards, Ann Arbor Mich. ©1952.
Shnayerson, N, A Finger Splint for Extension or Flexion; Jour. A.M.A. 6/18/38 pp. 2070-2071.

Primary Examiner—Robert W. Michell
Assistant Examiner—Arthur S. Rose
Attorney, Agent, or Firm—Duckworth, Allen, Dyer & Pettis

[57] ABSTRACT

A splint for use with the distal joint of a finger or thumb to control marked hyperextension of the joint. The splint is particularly useful in improving handwriting of persons experiencing such hyperextension by providing a preselected force urging the finger into flexion. A generally E-shaped frame is formed from spring steel wire with mutually parallel outer arm, central arm and inner arm connected by an outer side element and an inner side element. The side elements form an obtuse angle in the range of 120° to 130°. The arms are padded with the central arm pad disposed in the volar interphalangeal crease of the distal joint of the finger, the inner arm pad on the dorsal surface over the middle phalanx, and the outer arm pad on the dorsal surface over the distal phalanx. The angle of the side elements results in spring tension between the pads to resist hyperextension of the distal joint. When used as an aid for improving handwriting, the spring tension is preselected to produce a required force on the writing instrument when the fingers and thumb are in the normal prehensile grasp attitude.

4 Claims, 9 Drawing Figures

DISTAL JOINT FINGER SPLINT

BACKGROUND OF THE INVENTION

1. Field of the Invention

The present invention relates to splint type devices, and more particularly, to a finger splint for correction of marked hyperextension at a finger distal joint.

2. Description of the Prior Art

Written communication skills are extremely important in modern society and, in particular, during the educational process from grammar school through college. Some students who have been found to have learning disabilities also have illegible handwriting. Most remedial programs designed to solve handwriting problems for students have considered that the ability of the student to grasp the writing instrument and to maintain an acceptable grasp while writing are important elements. In the past, such programs have assumed that this elementary ability is present in the subject and have concentrated on the handwriting instrument, the paper, the position of the hand, and the formation of the letters. However, one of the co-inventors of the present invention, an occupational therapist, in observing learning disability students in Ormond Beach, Fla., discovered that many such students with poor handwriting do not demonstrate an acceptable grasp on the writing instrument and have difficulty in maintaining their grasp for even a short period of time. Further investigation of the joint posture of the digits directly involved in handwriting in these students revealed that one or more of the three interphalangeal joints used in grasping would bend back into marked hyperextension when pressure was applied to the writing instrument. Such marked hyperextension prevents the student from assuming the normal grasp and control necessary for handwriting. The therapist screened 80 problem students in three schools and found 33 of these students who exhibited marked hyperextension at the distal joints of thumbs and fingers. As discussed in *Hand Pain and Impairment*, Cailliet, Rene; Philadelphia; F. A. David Company, 1975, such marked hyperextension is considered an abnormality of the distal joint.

As a result of these observations, the therapist set up matched pairs of students as experimental and control groups to develop and evaluate a practical device for correcting the noted physical abnormality. The therapist determined that a simple finger splint having a carefully selected shape, size, and tension can provide support for fingers and thumbs having the noted hyperextension of the distal joint. An in-depth survey of medical literature and authorities on finger joints has failed to reveal either prior identification of this problem in handwriting or suitable appliances for correction of the problem. Similarly, investigation into the literature and authorities on penmanship and correction of unsatisfactory penmanship yielded a void in this area.

The only known commercially available appliance suitable for fingers is the "Spling" adjustable finger flexion orthosis manufactured by LBM Hand Rehab Products, Long Beach, Calif. This appliance is a splint designed for finger joints other than the distal joint and were found unsuitable for the present application. Thus, there exists a need for a small, light weight, flexible splint usable with the distal joints of the fingers and thumb to assist persons with the noted hyperextension to improve tasks involving the prehensile grasp.

SUMMARY OF THE INVENTION

As a result of the above described investigations and extensive experimental testing, a finger splint for correction of marked hyperextension at the distal joints of fingers and thumbs has been developed. The splint of the present invention uses a pad attached at right angles to the outer end of a spring-loaded lever arm. The other end of the arm is connected to a pivot point which may be disposed in or adjacent to the distal volar interphalangeal crease of the distal joint of a thumb or finger. This pivot is held in position by elements of the splint attached to the finger or thumb in the region of the middle or proximal phalanx. The pad at the outer end of the lever arm is disposed across the finger over the dorsal surface of the distal portion, preferably at the base of the fingernail, such that tension of the spring loaded lever arm urges the distal joint into flexion. The spring tension of the lever arm is preset to thus cause partial flexion of the distal joint when the finger is relaxed, and to prevent significant hyperextension when pressure is applied to a writing instrument by the volar surface of the distal portion of the finger or thumb.

One implementation of the splint of the invention is formed from a spring wire such as steel music wire, bent to have essentially the shape of an "E". Three arms of the splint, which would correspond to the horizontal strokes of an "E" are padded with rubber, plastic or other semirigid smooth material. One side element of the splint which would correspond to part of the vertical line of the "E" forms the spring loaded lever, with its pad at the forward end of the splint. The other side element connects the center arm, which acts as the pivot, to the pad at the rearward end of the splint for attaching to the middle portion of the finger to anchor the pivot. The forward and rearward side elements are bent with respect to the center arm so as to form an obtuse preset angle in the range of 120° to 130°.

The lengths of the straight elements of the splint may be tailored to the size of the finger or thumb with which it is to be used. In some applications, it may be preferable to custom build the splint of the invention to fit the particular individual. However, the splint can be manufactured in a series of standard sizes based on anthropometric studies of variations in human hands. The simplicity and the low cost of the invention will permit a variety of sizes to be readily available.

In use, the E-shaped splint is applied to the finger or thumb with the forward arm placed approximately at the base of the fingernail, the center arm along the distal volar interphalangeal crease, and the rearward arm on the dorsal surface of the finger approximately midway between the distal joint and the proximal joint. With the finger in a relaxed condition, the distal joint will be bent slightly. When pressure is applied to the volar surface of the distal portion of the finger tending to cause extension of the joint, the spring tension created by the splint of the invention will tend to prevent the hyperextension condition. When the splint is designed for improvement of handwriting, the required pressure on the writing instrument is determined and the splint wire diameter selected to provide sufficient writing pressure from the finger when normal joint extension is achieved with the splint in place. Such values of pressure have been found to be non-critical and an average individual generally can tolerate 6 ounces of force for up to 4 hours.

In accordance with the invention, the splints may be constructed for all affected fingers on a hand. In some instances, the problem may occur with only one finger or the thumb, while in other individuals, the problem may be present at all joints.

The use of the splint of the invention in experimental tests involving experimental groups and control groups revealed a significant improvement in handwriting skills in the tested group when before tests and control group tests were compared. Subjectively, many individuals taking part in the experiment noted a reduction or elimination of joint pain which has been experienced when attempting to write correctly without the splints.

It is therefore a principal object of the invention to provide an appliance for improvement of marked hyperextension of the distal joint of a thumb of finger.

It is another object of the invention to provide a splint type appliance of small size that may be worn on a finger or thumb without discomfort.

It is still another object of the invention to provide a finger splint for use by individuals having marked hyperextension of the distal joint of digits used for writing to assist the individual in improving handwriting skills.

It is yet another object of the invention to provide a finger splint which will relieve pain associated with hyperextension of distal joints and which will allow such individuals to grasp writing instruments in the normal prehensile grasp.

It is a further object of the invention to provide a finger splint wearable by individuals having hyperextension of the distal joint of the digits used in handwriting which will permit such individuals to easily write comfortably and legibly.

These and other objects and advantages of the invention will be evident from the following description when read in light of the drawings.

DETAILED DESCRIPTION OF THE PREFERRED EMBODIMENT

Figure 1:
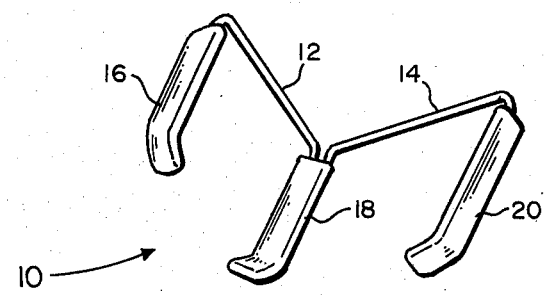
FIG. 1 is a perspective view of a finger splint in accordance with the invention.
Figure 2:
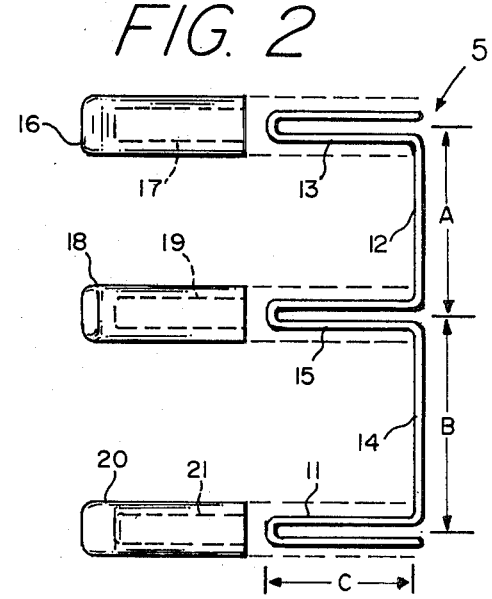
FIG. 2 is an exploded top view of the splint of FIG. 1 showing the wire frame and the pads in exploded view.
Figure 3:
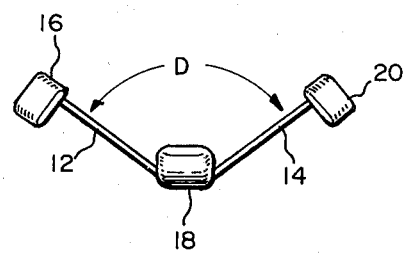
FIG. 3 is a side view of the splint of FIG. 1 viewed from the open end side.

Referring to FIG. 1, a perspective view of the preferred embodiment of the finger splint for correction of marked hyperextension at a finger distal joint is shown. It is to be understood that the splint shown generally at 10 illustrates the general configuration thereof and that the exact proportions of the splint may be tailored to the physical characteristics of the user. A spring frame, as seen in FIG. 2, is formed from an elastic material which may be, for example, spring steel wire, type A22A-63T. The spring wire is bent to form a generally "E" shaped form 5 having a forward arm 13, a central arm 15 and a rear arm 11 with a forward side piece 12 and a rearward side piece 14. Each arm is padded, such as pad 16 on forward arm 13, pad 18 on central arm 15, and pad 20 on rear arm 12. Pads 16, 18 and 20 may be formed from any firm, smooth material having slight resilience so as to provide comfort to the user of the splint. For example, a soft, thermoplastic tubing may be used which is slipped on the arm and molded to the shape shown by means of a heat press. For such material, the outer tips will close and are preferably bent as seen in FIG. 1 to assist in maintaining the splint on the user's finger. Thus, as indicated in FIG. 2, each pad 16, 18, 20 has a respective interior opening, 17, 19 and 21. As will be obvious to those skilled in the art, a variety of materials may be effectively utilized for pads 16, 18 and 20. Referring to FIG. 1 and FIG. 3, spring wire frame 5 is prebent to a selected angle, shown as D in FIG. 3 which is a view of the splint from the open side.

Splints 10 may be designed and constructed to fit the distal joints of the fingers and the thumbs of individuals having marked hyperextension at the digital joints of their thumbs and fingers. An important application of the splint 10 is in retraining of persons unable to properly hold writing instruments due to such abnormalities of their joints to correct or improve their handwriting. After retraining, splints 10 may then be further used to permit such individuals to write more easily, comfortably and legibly. For such application, the primary joints of interest are those of the thumb, the index finger and the middle finger. It is preferable to tailor the design of splints for each digit based on the pressures required from each digit during handwriting. For purposes of illustration, the use of splint 10 on an index finger and on a thumb are illustrated on FIGS. 4 and 5.

As is evident, the actual pressure or force on a writing instrument is generally the summation of the force from the thumb and the forefinger. A portion of forces applied by these digits is utilized in gripping the instrument and the remainder in pressure on the writing surface.

Figure 4:
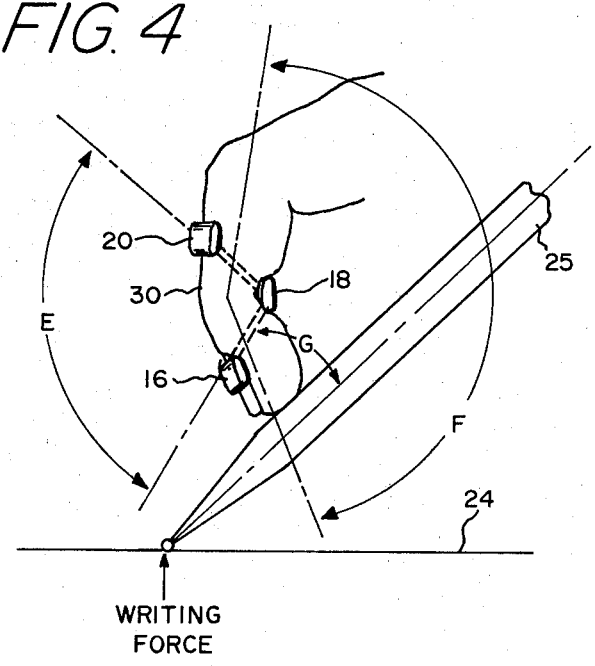
FIG. 4 is a perspective view of the splint of FIG. 1 on place of an index finger showing a normal operative relationship with a writing instrument.

Turning first to FIG. 4, an index finger 30 is shown on contact with a writing instrument 25 held at a typical writing angle with paper 24. As may be noted, splint 10 is being worn on finger 30 with forward pad 16 in contact with the fingernail close to its root, rear pad 20 in contact with the dorsal surface of the index finger between the distal and the proximal joints, and central pad 18 bears into the distal volar crease of the distal joint. A typical writing force of instrument 25 on paper may be on the order of 0.44 lbs. To provide assistance for finger 30 in applying its component of such force to writing instrument 25, the diameter of the spring wire forming spring wire frame 5 and the size of the prebend angle D are variables. Also, involved is the length A of side element 12 noted in FIG. 2 which represents a lever arm as the joint is extended against rear arm 14. Rear side element 14 and pad 20 serve to maintain pad 18 fixed relative to the distal joint when the distal joint of finger 30 in FIG. 4 is in its full extension. As is normally desirable for writing, the angle E may be, for example, approximately 115°. Knowing the length of forward side element 12 which forms a moment arm with respect to the central arm 15, and the diameter of the spring wire, the prebent angle can be calculated for a particular writing force. It has been found, in this example, that 21 gauge music wire with an approximate prebent angle D of 128° will produce a moment of 3.5 oz.-inches at full extension with an angle G of about 60° between the writing instrument 25 and the tip of finger 30, and is sufficient to prevent hyperextension of the distal joint of finger 30 and allowing the user to apply the desired pressure for writing. The design is preferably made for a worst case condition such as the use of a ball point pen which may require more force than a lead pencil or straight pen.

Figure 5:
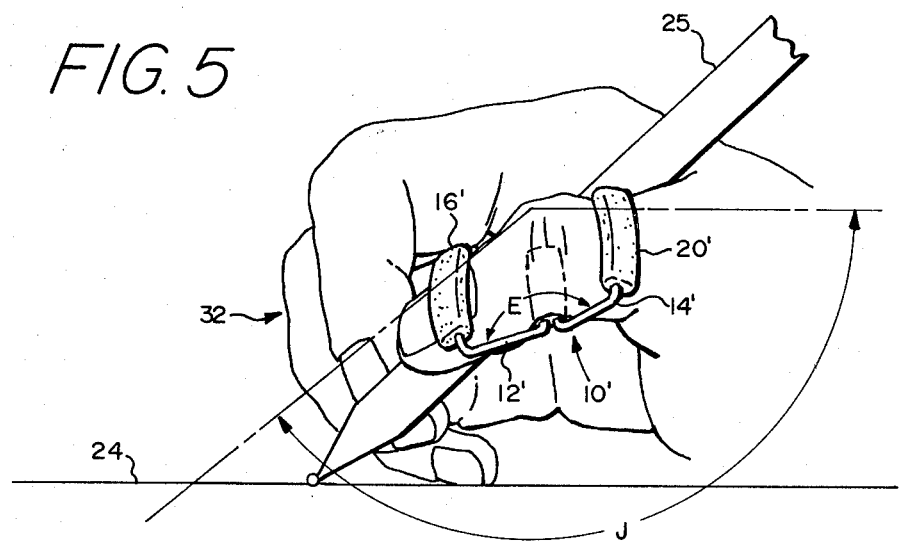
FIG. 5 is a perspective view of the splint of FIG. 1 in operative position on a thumb while holding a pencil in the prehensile grasp.

FIG. 5 illustrates a hand shown generally at 32 holding a writing instrument 25 in the preferred prehensile grasp for handwriting. A splint for the thumb shown generally at 10' is being worn with the side elements 12' and 14' worn on the outer surface of the thumb to minimize interference with writing instrument 25. Typical angles of operation are shown with angle J indicating the joint angle of the thumb which is about 135° in this example. Splint 10', when normal grasping and writing pressure is applied by the thumb to writing instrument 25, will have an operative angle E of about 123°. From the value of the operative angle, knowledge of the length of side element 12', and a selection of force to be applied by the thumb, the diameter of the spring wire in splint 10' and the preset angle D may be determined.

Many factors in an individual may be considered in the design and application of the invention such as: degree of hyperextension; specific digits involved; types of writing instruments to be used; most comfortable grasping posture of the hand; degree of flexure; and sizes of digits. The major design variables are therefore the lengths of the splint elements, the spring constant of the wire and the prebend angle. Although it is thus preferable to tailor splints to an individual, it is also possible to produce the devices in a range of stock sizes. As an example, in experimental work with eighth and ninth grade students, the following three sizes of the splints shown in FIGS. 1, 2, and 3 were found suitable:

| SIZE | A | B | C | D |
|------|------|------|------|------|
| Small | 0.45" | 0.53" | 0.7" | 128° |
| Medium | 0.53" | 0.62" | 0.75" | 128° |
| Large | 0.60" | 0.70" | 0.8" | 128° |

To vary the restraining force of the splint, prebend angle D may be slightly changed with pliers to suit a particular individual.

ALTERNATIVE EMBODIMENTS

Figure 6:
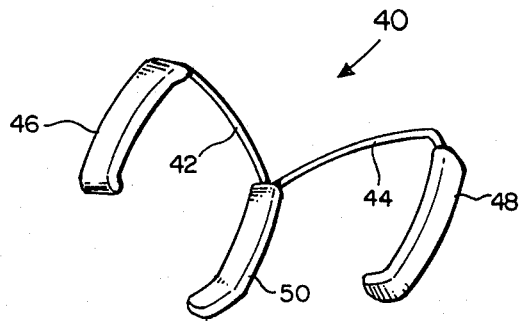
FIG. 6 is a perspective view of an alternative embodiment of the invention having elements curved to fit the digit.
Figure 7:
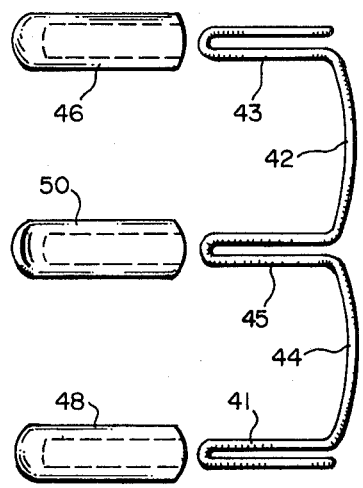
FIG. 7 is an exploded view of the embodiment of FIG. 6.

Although the preferred embodiment heretofore described may be made economically and will provide a satisfactory splint for most application, a number of alternative embodiments will be obvious and may provide desirable in certain instances. For example, turning to FIGS. 6 and 7, a variation in the design of the splint of FIG. 1 is shown generally at 40 which may be tailored to the contours of an individual's fingers. As may be noted the finger surface contacting pads 46, 50 and 48 are curved to match the contour of the fingers and the spring wire side elements 42 and 44 are similarly curved to match the curvature of the lateral surfaces of the fingers. This design can therefore be worn with more comfort to the user and, advantageously, may be used for longer periods of time.

Figure 8:
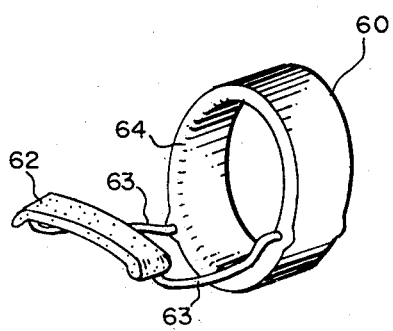
FIG. 8 is a perspective view of another embodiment.
Figure 9:
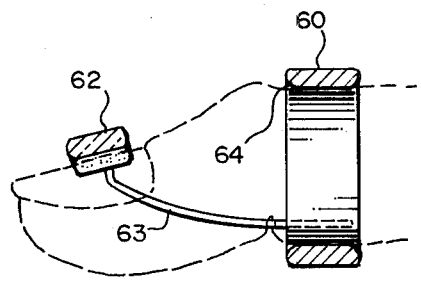
FIG. 9 is a cross sectional view of the splint of FIG. 8.

As may be understood the rear pad 20 and side element 14 of the device as shown in FIG. 1 connect with the dorsal surface between the distal and proximal joints to provide support for pad 18 at the distal lower digital crease. Pad 18 acts as a pivot point for the forward spring element 12 and pad 16. Thus other designs are practical, and may be desirable in some instances, in which other structures are provided to form such pivot points. For example, in FIGS. 8 and 9 a ring-type support for the spring arm and pad is shown. Ring 60 is sized to fit snugly around the finger between the distal and proximal joints. Spring arms 63 are cantilevered out from ring 60 to support pad 62 which is in contact with the surface of a fingernail. This embodiment of the invention has the advantage of maintaining proper alignment of pad 62 under activities which involve extensive flexing of the distal joint. As best seen in the cross-sectional view of FIG. 9, ring portion 60 has its inner corners 64 rounded and smoothed to minimize discomfort under maximum extension of the joint. Ring 60 may preferably be formed from aluminum for lightness and smoothness of the finger contracting surfaces.

The splint of the invention herein disclosed provides a low cost, simple and effective device for use by persons having hyperextension of the distal joints of the digits. The invention is particularly suitable for improving handwriting skills in such individuals and for assisting such individuals in performing other manual tasks where moderate pressures need to be applied by the fingertips.

Several embodiments of the invention have been described in detail hereinabove, which are intended for exemplary purposes only. Variations in construction and materials will be obvious to those or ordinary skill in the art and such variations are considered to fall within the spirit and scope of the invention.

We claim:

1. A splint for use with an index finger which exhibits hyperextension of a distal joint thereof to permit control of the finger during handwriting, comprising:

a frame having an elongated outer arm with first and second ends, an elongated central arm with first and second ends, and an elongated inner arm with first and second ends, said arms being arranged in parallel relationship with each other, an elongated outer side element having first and second ends, said first end of said outer side element being connected to said first end of said outer arm, said second end of said outer side element being connected to said first end of said central arm, an elongated inner side element having first and second ends, said first end of said inner side element being connected to said first end of said central arm, said second end of said inner side element being connected to said first end of said inner arm, said arms and said side elements forming essentially an E-shape, said frame being otherwise open, said frame being fabricated from a single continuous spring steel wire and having said outer side element and the inner side element bent to form an obtuse angle therebetween;

an outer pad disposed over said outer arm for contacting a dorsal surface of said index finger over the distal phalanx;

a central pad disposed over said central arm for contacting the volar interphalangeal crease of the distal joint of said finger; and an inner pad disposed over said inner arm for contacting the dorsal surface of said finger over the middle phalanx thereof;

whereby when said splint is disposed on said index finger, said outer pad cooperates with said spring wire side elements to urge said finger into flexion.

2. The splint as defined in claim 1 in which said outer pad, said central pad, and said inner pad are curved to essentially conform to the surfaces of the finger contacted by said pads; and said outer side element and said inner side element are curved to conform to the lateral surfaces of said finger.

3. A splint as defined in claim 1 in which said obtuse angle of said two side elements has an angle in the range of 120° to 130°.

4. The splint as defined in claim 1 in which said obtuse angle of said two side elements and the spring constant of said spring steel wire are selected to provide a preselected force tending to urge said finger into flexion.

* * * * *